US012053364B2

(12) United States Patent
Dvir et al.

(10) Patent No.: US 12,053,364 B2
(45) Date of Patent: Aug. 6, 2024

(54) IMPLANTS WITH ENHANCED SHELL ADHESION

(71) Applicant: G & G BIOTECHNOLOGY LTD, Haifa (IL)

(72) Inventors: Haim Dvir, Nesher (IL); Dael Govreen-Segal, Haifa (IL); Wesley Allen Schultz, Aschaffenburg (DE)

(73) Assignee: G & G BIOTECHNOLOGY LTD, Haifa (IL)

(*) Notice: Subject to any disclaimer, the term of this patent is extended or adjusted under 35 U.S.C. 154(b) by 244 days.

(21) Appl. No.: 16/645,793

(22) PCT Filed: Feb. 18, 2019

(86) PCT No.: PCT/IL2019/050194
§ 371 (c)(1),
(2) Date: Mar. 10, 2020

(87) PCT Pub. No.: WO2019/159182
PCT Pub. Date: Aug. 22, 2019

(65) Prior Publication Data
US 2021/0361402 A1    Nov. 25, 2021

Related U.S. Application Data

(60) Provisional application No. 62/631,937, filed on Feb. 18, 2018.

(51) Int. Cl.
A61F 2/00     (2006.01)
A61L 27/18    (2006.01)
A61L 27/26    (2006.01)
A61L 27/52    (2006.01)
C08L 83/04    (2006.01)

(52) U.S. Cl.
CPC ............ A61F 2/0059 (2013.01); A61L 27/18 (2013.01); A61L 27/26 (2013.01); A61L 27/52 (2013.01); C08L 83/04 (2013.01); A61L 2430/04 (2013.01); C08L 2312/00 (2013.01)

(58) Field of Classification Search
CPC ............. A61F 2210/0076; A61L 27/44; C08L 2312/00
See application file for complete search history.

(56) References Cited

U.S. PATENT DOCUMENTS

| 2,676,892 A | 4/1954 | McLaughlin |
| 2,797,201 A | 6/1957 | Veatch |
| 3,030,215 A | 4/1962 | Veatch |
| 3,189,662 A | 6/1965 | Vaughn, Jr. |
| 3,230,184 A | 1/1966 | Alford |
| 3,247,158 A | 4/1966 | Alford |
| 3,308,491 A | 3/1967 | Spence |
| 3,548,420 A | 12/1970 | Spence |
| 3,622,437 A | 11/1971 | Hobaica |
| 3,681,787 A | 8/1972 | Perras |
| 3,683,424 A | 8/1972 | Pangman |
| 3,811,133 A | 5/1974 | Harris |
| 3,986,213 A | 10/1976 | Lynch |
| 4,019,209 A | 4/1977 | Spence |
| 4,021,589 A | 5/1977 | Copley |
| 4,072,635 A | 2/1978 | Jeram |
| 4,298,998 A | 11/1981 | Naficy |
| 4,380,569 A | 4/1983 | Shaw |
| 4,455,691 A | 6/1984 | Van Aken Redinger |
| 4,459,145 A | 7/1984 | Elsholz |
| 4,470,160 A | 9/1984 | Cavon |
| 4,650,889 A | 3/1987 | Plueddemann |
| 4,676,795 A | 6/1987 | Grundei |
| 4,681,587 A | 7/1987 | Eberl |
| 4,773,909 A | 9/1988 | Chaglassian |
| 4,795,464 A | 1/1989 | Eberl |
| 4,849,456 A | 7/1989 | Champion |
| 4,861,804 A | 8/1989 | Nakanishi |
| 4,992,312 A | 2/1991 | Frisch |
| 5,011,494 A | 4/1991 | Von |
| 5,055,497 A | 10/1991 | Okada |
| 5,081,997 A | 1/1992 | Bosley, Jr. |
| 5,147,398 A | 9/1992 | Lynn |
| 5,171,269 A | 12/1992 | Bark |
| 5,202,362 A | 4/1993 | Hermele |
| 5,236,454 A | 8/1993 | Miller |
| 5,246,454 A | 9/1993 | Peterson |
| 5,258,578 A | 11/1993 | Smith |

(Continued)

FOREIGN PATENT DOCUMENTS

| CN | 1303716 A | 7/2001 |
| CN | 2457979 Y | 11/2001 |

(Continued)

OTHER PUBLICATIONS

CN 102949251 B (Google translation to English, downloaded Jul. 2022) (Year: 2022).*
Leow et al (Prosthetics and Orthotics International, 1999, vol. 23, pp. 169-173) (Year: 1999).*
Medsafe (New Zealand Medicines and Medical Devices Safety Authority, Silicone Breast Implants, Revised 2013, https://www.medsafe.govt.nz/hot/alerts/silicon.asp) (Year: 2013).*
Arkaban et al (Polymers, 2022, vol. 14, pp. 1-33) (Year: 2022).*
Bu et al (Am J Transl Res, 2021, vol. 13, pp. 11439-11449) (Year: 2021).*
Extended European Search Report for App. No. EP19753959.6, dated Oct. 15, 2021, 10 pages.
"Bondurant, Stuart, et al. Silicone implants and breast imaging. 1999. Retrieved from URL: http://www.ncbi.nlm.nih.gov/books/NBK44781/01 Jan 1999 (Jan. 1, 1999) chapter 12", 308 pages.

(Continued)

Primary Examiner — Mark V Stevens
(74) Attorney, Agent, or Firm — GRAESER ASSOCIATES INTERNATIONAL INC.; D'Vorah Graeser

(57) ABSTRACT

A prosthetic implant, suitable for implantation to the human body, comprising a shell and a gel filling, wherein the shell comprises an innermost layer and at least an additional layer; wherein the innermost layer is in contact with the gel; wherein the innermost layer is adapted to adhere to said gel.

22 Claims, 4 Drawing Sheets

(56) References Cited

U.S. PATENT DOCUMENTS

| | | |
|---|---|---|
| 5,358,521 A | 10/1994 | Shane |
| 5,407,445 A | 4/1995 | Tautvydas |
| 5,480,430 A | 1/1996 | Carlisle |
| 5,496,367 A | 3/1996 | Fisher |
| 5,534,023 A | 7/1996 | Henley |
| 5,545,217 A | 8/1996 | Offray |
| 5,549,671 A | 8/1996 | Waybright |
| 5,590,430 A | 1/1997 | Sereboff |
| 5,653,755 A | 8/1997 | Ledergerber |
| 5,658,330 A | 8/1997 | Carlisle |
| 5,723,006 A | 3/1998 | Ledergerber |
| 5,741,877 A | 4/1998 | Tiffany |
| 5,779,734 A | 7/1998 | Ledergerber |
| 5,824,081 A | 10/1998 | Knapp |
| 5,871,497 A | 2/1999 | Young |
| 5,902,335 A | 5/1999 | Snyder |
| 6,146,418 A | 11/2000 | Berman |
| 6,183,514 B1 | 2/2001 | Becker |
| 6,187,043 B1 | 2/2001 | Ledergerber |
| 6,194,476 B1 | 2/2001 | De |
| 6,271,278 B1 | 8/2001 | Park |
| 6,296,800 B1 | 10/2001 | Stelter |
| 6,387,981 B1 | 5/2002 | Zhang |
| 6,464,726 B1 | 10/2002 | Heljenek |
| 6,478,656 B1 | 11/2002 | Khouri |
| 6,486,237 B1 | 11/2002 | Howe |
| 6,544,287 B1 | 4/2003 | Johnson |
| 6,733,893 B2 | 5/2004 | Suzuki |
| 6,835,763 B2 | 12/2004 | Ellis |
| 6,932,840 B1 | 8/2005 | Bretz |
| 6,967,221 B2 | 11/2005 | Meguriya |
| 6,972,313 B2 | 12/2005 | Howe |
| 7,988,731 B2 | 8/2011 | Govrin-Yehudian |
| 9,339,371 B2 * | 5/2016 | Dvir ............ A61F 2/12 |
| 9,452,043 B2 | 9/2016 | Govrin-Yehudian |
| 9,775,703 B2 | 10/2017 | Govreen-Segal |
| 10,052,191 B2 | 8/2018 | Govrin-Yehudian |
| 10,213,293 B2 | 2/2019 | Dvir |
| 10,933,165 B2 | 3/2021 | Govreen-Segal |
| 2001/0054224 A1 | 12/2001 | Corbin |
| 2002/0038147 A1 | 3/2002 | Miller |
| 2002/0103539 A1 | 8/2002 | Stelter |
| 2002/0193878 A1 | 12/2002 | Bowman |
| 2003/0047718 A1 | 3/2003 | Narayan |
| 2003/0074084 A1 | 4/2003 | Nakao |
| 2003/0127090 A1 | 7/2003 | Gifford |
| 2003/0135255 A1 | 7/2003 | Sundar |
| 2003/0144411 A1 | 7/2003 | Howe |
| 2003/0153244 A1 | 8/2003 | Chen |
| 2004/0049269 A1 | 3/2004 | Corbitt |
| 2004/0060563 A1 | 4/2004 | Rapacki |
| 2004/0073305 A1 | 4/2004 | Schneider-Nieskens |
| 2004/0153151 A1 | 8/2004 | Gonzales |
| 2005/0052414 A1 | 3/2005 | Park |
| 2005/0123627 A1 | 6/2005 | Hagen |
| 2005/0197698 A1 | 9/2005 | Schneider-Nieskens |
| 2005/0252414 A1 | 11/2005 | Craig |
| 2006/0025859 A1 | 2/2006 | Stelter |
| 2006/0136056 A1 | 6/2006 | Wohl |
| 2006/0161266 A1 | 7/2006 | Schwibner |
| 2006/0224239 A1 | 10/2006 | Tiahrt |
| 2007/0050026 A1 | 3/2007 | Carvallo |
| 2007/0050027 A1 | 3/2007 | McGhan |
| 2007/0093894 A1 | 4/2007 | Darouiche |
| 2007/0135916 A1 | 6/2007 | Maxwell |
| 2007/0293945 A1 | 12/2007 | Snyder |
| 2008/0033522 A1 | 2/2008 | Grewe |
| 2008/0203263 A1 | 8/2008 | Carnevali |
| 2009/0022808 A1 * | 1/2009 | Champion ............ A61K 31/728 424/491 |
| 2009/0030515 A1 * | 1/2009 | Schuessler ............ A61F 2/12 623/8 |
| 2009/0048480 A1 | 2/2009 | Klenk |
| 2009/0054985 A1 | 2/2009 | Anderson |
| 2009/0270985 A1 | 10/2009 | Schuessler |
| 2009/0292362 A1 | 11/2009 | Allard |
| 2009/0299472 A1 | 12/2009 | Huang |
| 2009/0299473 A1 | 12/2009 | Govrin-Yehudian |
| 2010/0158980 A1 | 6/2010 | Kopczynski |
| 2010/0268282 A1 | 10/2010 | Trieu |
| 2010/0330011 A1 * | 12/2010 | Kennan ............ C08L 83/12 424/59 |
| 2011/0060411 A1 | 3/2011 | Govrin-Yehudian |
| 2011/0146361 A1 | 6/2011 | Davidson |
| 2011/0182957 A1 | 7/2011 | Nicoll |
| 2011/0196488 A1 | 8/2011 | Goraltchouk |
| 2012/0277860 A1 * | 11/2012 | Dvir ............ A61L 27/446 427/2.24 |
| 2012/0323339 A1 | 12/2012 | Olalde Graells |
| 2013/0110243 A1 | 5/2013 | Patterson |
| 2013/0211518 A1 * | 8/2013 | Boegershausen ............ A61F 2/12 623/8 |
| 2014/0236299 A1 | 8/2014 | Roeder |
| 2015/0072018 A1 | 3/2015 | Rosines |
| 2015/0305853 A1 | 10/2015 | Schuessler |
| 2016/0143943 A1 * | 5/2016 | Ohno ............ C08B 37/0072 424/493 |
| 2016/0175486 A1 | 6/2016 | Govreen-Segal |
| 2017/0128192 A1 | 5/2017 | Govrin-Yehudian |
| 2018/0000991 A1 | 1/2018 | Govreen-Segal |
| 2018/0036116 A1 | 2/2018 | Govreen Segal |
| 2021/0244856 A1 | 8/2021 | Govreen-Segal |

FOREIGN PATENT DOCUMENTS

| | | | |
|---|---|---|---|
| CN | 103068413 A | 4/2013 | |
| CN | 203107780 U | 8/2013 | |
| CN | 104039366 | 9/2014 | |
| CN | 102949251 B * | 12/2016 | ............ A61F 2/12 |
| CO | 7350629 A2 | 8/2015 | |
| EP | 0821575 A1 | 2/1998 | |
| EP | 0874604 A1 | 11/1998 | |
| EP | 1432562 A1 | 6/2004 | |
| EP | 1663072 A2 | 6/2006 | |
| EP | 2210971 | 7/2010 | |
| EP | 2962662 | 1/2016 | |
| JP | 2002296940 A | 10/2002 | |
| RU | 2197509 C1 | 1/2003 | |
| RU | 2233644 | 8/2004 | |
| RU | 2233644 C1 | 8/2004 | |
| WO | 9632908 A1 | 10/1996 | |
| WO | 9719654 A1 | 6/1997 | |
| WO | 9726025 A1 | 7/1997 | |
| WO | 03026866 A1 | 4/2003 | |
| WO | 2005020843 A2 | 3/2005 | |
| WO | 2005086067 | 9/2005 | |
| WO | 2006069677 A2 | 7/2006 | |
| WO | 2006114786 A2 | 11/2006 | |
| WO | 2006133366 A1 | 12/2006 | |
| WO | 2009018105 | 2/2009 | |
| WO | 2011086537 | 7/2011 | |
| WO | 2011086537 A2 | 7/2011 | |
| WO | 2013015987 | 1/2013 | |
| WO | 2013070290 A1 | 5/2013 | |
| WO | WO-2017184962 A1 * | 10/2017 | ............ A61F 2/12 |
| WO | WO-2017196973 A2 * | 11/2017 | ............ A61F 2/0077 |
| WO | 2020072103 | 4/2020 | |

OTHER PUBLICATIONS

Bondurant, Stuart et al., "Silicone implants and breast imaging.", (19990000), pp. 264-284, URL: http://www.ncbi.nlm.nih.gov/books/NBK44781, (Jan. 1, 1999) 559 pages.

Brazilian Office Action for App. No. BR1120170194317, dated Jun. 9, 2020, 4 pages.

Brazilian Office Action for BR1120120175360 dated Oct. 8, 2018, 13 pages.

Chinese Office Action dated Oct. 9, 2018 issued in CN Patent Application No. 201680015309.5, dated Oct. 9, 2018, 3 pages.

Chinese Office Action for Application No. 201680015309.5, dated Jun. 21, 2019, 10 pages.

(56) References Cited

OTHER PUBLICATIONS

Columbian Office Action issued in CO Application No. NC2017/0010151, dated Feb. 2, 2019, 9 pages.
Combined Search Report and Written Opinion for parent PCT Application No. PCT/182011/050217, mailed Jul. 5, 2011 (14 pages).
Guarding against potential inhibitors /poisons of platinum catalyzed addition cure release coatings' published by Dow-Corning as part of their 'Facts on File Series', published in 2003 (3 pages).
Ishida, Hatsuo. "Controlled interphases in glass fiber and particulate reinforced polymers: Structure of silane coupling agents in solutions and on substrates." The interfacial interactions in polymeric composites. Springer Netherlands, 1993. 169-199. 31 pages.
Japanese Office Action (with English language translation) for Application No. JP2017-566230, dated Feb. 10, 2020, 7 pages.
JP2002296940—English-translation (17 pages).
Moyer, Hunter R. M.D.; Ghazi, Bahair H. M.D.; Losken, Albert M.D. "The Effect of Silicone Gel Bleed on Capsular Contracture: A Generational Study" Plastic and Reconstructive Surgery: Oct. 2012—vol. 130—Issue 4—p. 793-800.
Notice of Allowance dated Apr. 21, 2020 for U.S. Appl. No. 15/701,883 (pp. 1-8).
Notice of Allowance dated Aug. 5, 2020 for U.S. Appl. No. 15/701,883 (pp. 1-9).
Notice of Allowance dated May 9, 2018 for U.S. Appl. No. 15/249,352 (pp. 1-7).
Notice of Allowance dated Oct. 17, 2018 for U.S. Appl. No. 15/686,457 (pp. 1-10).
Office Action dated Feb. 21, 2020 for U.S. Appl. No. 15/701,883 (pp. 1-5).
Office Action dated Jul. 13, 2018 for U.S. Appl. No. 15/686,457 (pp. 1-6).
Office Action dated Nov. 1, 2017 for U.S. Appl. No. 15/249,352; (pp. 1-9).
Office Action for corresponding Chinese Application No. 201190000276.X, mailed Nov. 7, 2012, provided with translation. (4 pages).
Office action for corresponding EP application 06728299.6, Issued Sep. 1, 2011 (4 pages).
Office action for corresponding EP application 06728299.6, Issued Jan. 20, 2011 (3 pages).
PEEK Biomaterials in Trauma, Orthopedic, and Spinal Implants. Biomaterials. 2007;28(32):4845-4869.
Russian Office Action for Application No. 2017132258, dated Jan. 13, 2020, 5 pages.
Russian Office Action for Application No. 2017132258, dated Aug. 23, 2019, 11 pages.
Russian Search Report for Application No. 2017132258, dated Aug. 15, 2019, 3 pages.
Search report for corresponding EP application 06728299.6, Issued Feb. 22, 2010. (9 pages).
Search report for related PCT/IL06/00501 issued Jan. 9, 2008 (7 pages).
Govrin-Yehudain et al., Five Year Safety and Satisfaction With the Lightweight Breast Implant, Aesthet Surg J., Feb. 10, 2021, 45 pages.
Govrin-Yehudain et al., Reduced Pain and Accelerated Recovery Following Primary Breast Augmentation With Lightweight Breast Implants, Aesthetic Surgery Journal, 2018, vol. 38(10) 1092-1096.
Jacky Govrin-Yehudain et al., Lightweight Breast Implants: A Novel Solution for Breast Augmentation and Reconstruction Mammaplasty, Aesthetic Surgery Journal, 2015, vol. 35(8) 965-971.
Norris et al., The Kinematics of Breasts Implanted With a Reduced Mass Implant: A Pilot Study, Aesthetic Surgery Journal, 2020, vol. 40(5) NP253-NP262.
Columbian Office Action (including English translation) issued in App. No. NC2017/0010151, dated Apr. 12, 2022, 18 pages.
Columbian Office Action issued in App. No. NC2017/0010151, dated Jun. 22, 2021, 9 pages.
Indian Office Action for App. No. IN201727036184, dated Jul. 27, 2021, 5 pages.
Office Action (including English translation) for App. No. IL254462, dated Aug. 30, 2020, 5 pages.
English language Japanese Office Action for App. No. JP2017-566230, dated Sep. 8, 2020, 5 pages.
Notice of Allowance dated Oct. 20, 2020 for U.S. Appl. No. 15/701,883 (pp. 1-8).
Corrected Notice of Allowability dated Feb. 3, 2021 for U.S. Appl. No. 15/701,883 (pp. 1-2).
Brazilian Office Action (including English translation) issued in App. No. BR112020015153, dated Apr. 4, 2023, 9 pages.
Canadian Office Action issued in App. No. CA2979385, dated Feb. 9, 2023, 4 pages.
English translation of Office Action issued in App. No. IL276645, dated Jun. 7, 2023, 5 pages.
Office Action (Non-Final Rejection) dated Jun. 7, 2023 for U.S. Appl. No. 17/153,925 (pp. 1-11).
Chinese Office Action (including English translation) issued in App. No. CN201980013791.2, dated Jul. 26, 2023, 10 pages.
https://silicone.co.uk/news/how-does-silicone-stick-to-different-surfaces/ Jun. 2, 2015.
Korean Office Action issued in App. No. KR10-2020-7022014, dated Oct. 23, 2023, 5 pages.
Office Action (Final Rejection) dated Dec. 6, 2023 for U.S. Appl. No. 17/153,925 (pp. 1-12).
Office Action dated Sep. 22, 2023 for U.S. Appl. No. 17/381,773 (pp. 1-9).
Soder et al. Plastic and Reconstructive Surgery 2009 123:1440-1451 (Year: 2009).
US Office Action for U.S. Appl. No. 16/643,793, filed Sep. 28, 2023.

\* cited by examiner

IMPLANTS WITH ENHANCED SHELL ADHESION

FIELD OF THE INVENTION

The present invention relates generally to implantable prosthetic devices and specifically to implantable prosthetic devices featuring improved adhesion of adjacent materials within these devices.

BACKGROUND OF THE INVENTION

In the last century reconstructive and cosmetic surgery has become a common practice and generally involves insertion of an implant to increase the size of an appendage, to correct asymmetries, change shape and fix deformities.

The standard implants used today comprise an outer shell typically formed from vulcanized silicone rubber (elastomer) and an inner content typically formed from silicone gel. A common problem with such implants is that the silicone elastomer of the shell and the silicone gel, when placed adjacent to one another, lack adequate adhesion properties.

The elastomeric shell is typically manufactured prior to filling using dip coating, spray coating, molding, or other known processes to create a shell with a desired thickness. For example, for manufacture of breast implants, the most common process is dip coating with the shell comprising several elastomeric layers; at least two silicone layers primarily for mechanical purposes and at least one internal silicone layer serving as a barrier to low molecular weight silicone moieties. In a typical manufacturing process, the shell is filled with liquid silicone which is cured into silicone gel to form the breast implant. Both the elastomeric and gel silicone follow addition reaction curing in the presence of a catalyst which is usually platinum based. The addition reaction involves platinum catalyzed reaction of vinyl functionalized (e.g. terminated or side grouped) silicones with hydrogen functionalized (e.g. terminated or side grouped) silicones.

The elastomeric shell and the content gel exhibit low adhesion as silicone in essence is an inert material. In addition, both the elastomeric shell and the gel are cross-linked networks which prefer to retain their own shape under external load, manifested as cohesive strength over adhesive strength and the two will tend to separate at the interface. The low adhesion between the shell and the gel may occur immediately after curing or alternatively after a period of time as the shell and the gel filling separate and a void filled with gas, typically air, or liquid is formed between them. The separation of shell and filler due to low adhesion can result in rupture of the shell due to abrasion of the detached shell and/or unwanted visible aesthetic changes to the implant area caused by the deformed shape of the separated implant.

The lack of adequate adhesion between the silicone elastomeric shell and silicone gel also exists in systems where the silicone gel is enhanced with additives to increase the cohesive strength of the gel. The shell and the enhanced silicone gel may separate at the interface due to the increased cohesive strength of the filler over the adhesive strength between the shell and gel.

Therefore there is an urgent need for an implant with an enhanced shell/content adhesion.

SUMMARY OF THE INVENTION

The present invention overcomes the deficiencies of the background art by providing an implant which has improved adhesion between the implant shell and the implant filling material/gel. The present invention proposes one or more of the following mechanisms to increase adhesion. It should be noted that while the mechanisms cited below describe exemplary materials such as silicone gel and elastomers, these mechanisms also refer to polymers in general and the materials cited herein should not be considered limiting. The present invention proposes one or more of the following mechanisms to increase adhesion:

The innermost layer of the shell comprises a lower ratio of a crosslinker to base polymer compared with other shell layers such that a network in formed between excess base in the shell that reacts with the excess crosslinker in the gel to form an adhesive bond between the shell and gel. As a non-limiting example the innermost layer of the shell comprises a lower ratio of hydrogen functionalized silicone to vinyl functionalized silicone compared with other shell layers such that a network in formed between excess base vinyl silicones in the innermost layer shell that react with the excess hydrogen crosslinker in the gel to form adhesive bond between the shell and gel.

Alternatively the innermost layer of the shell comprises chains with bi or poly-functional groups and chains with a single functional group such as vinyl functional group.

The single functional group chains effectively compete for the excess hydrogen crosslinker silicone, resulting in an excess of base vinyl silicones in the innermost shell layer to react with excess hydrogen crosslinker in the gel to form an adhesive bond between the shell and gel.

Alternatively the innermost layer of the shell comprises a mixed ratio of silicone elastomer and silicone gel to provide an intermediate material that is more compatible to both the elastomer shell and the filling gel thereby improving adhesion to both gel and elastomer. Alternatively the innermost layer of the shell is wet with one part of the gel which is then allowed to diffuse to some extent into the innermost layer of the shell or beyond over an extended period of time, for example but without intention to be limiting, for up to a few days before the next steps of filling and curing. During the curing process the excess of this one part of the gel that has diffused into the innermost layer reacts with the curing gel and improves the adhesion between the gel and shell.

Alternatively a bi-component room temperature vulcanized (RTV) elastomer is used as the adhesion promoter between shell and gel. One component is incorporated into the innermost layer's elastomer composition as part of the shell manufacturing. The shell is filled with the liquid Silicone containing the other component and upon contact with the shell the two components react and create adhesion between the shell and gel.

Alternatively a bi-component room temperature vulcanized (RTV) elastomer is used as the adhesion promoter between shell and gel. One component is used to wet the shell and allowed to diffuse to some extent into the internal layers of the shell for an extended period of time, for example but without intention to be limiting, for up to a few days before the next steps of filling and curing. The shell is filled with the liquid Silicone containing the other component and upon contact with the shell the two components react and create adhesion between the shell and gel.

Alternatively, the innermost layer of the shell is structured such that the topography of the innermost layer features irregularities to improve adhesion of the gel to the shell. The surface irregularity results in improved adhesion via different mechanisms combining mechanical and chemical interactions such as mechanical interlocking, wetting properties such as lotus effect mechanism and weak van der Waals (VDW) interactions to strong chemical bonds. Preferably irregularities are such that the outer shell remains largely unaffected, for example in terms of appearance (e.g. smoothness).

Surface topography may be determined by different methods such as imprinting, creating a negative on the mold or mandrel surface, modifying the outermost layer of the shell and then inside-outing it, adding volatile or soluble elements on the surface that are later removed and similar methods.

Alternatively, the innermost layer of the shell is resurfaced such that the topography and/or chemical nature of the internal layer are altered to improve adhesion of the gel to the shell. The resurfacing results in improved adhesion via different mechanisms such as mechanical interlocking, wetting properties such as lotus effect mechanism and chemical adhesion improvement for chemical interactions on the surface ranging from weak van der Waals (VDW) interaction to strong chemical bonds; Some methods of resurfacing include mechanical etching or chemical etching, both of which can be achieved using high energy sources such as plasma or laser.

Alternatively, prefabricated connection elements (e.g. fibers or hooks) may be integrated partially into the shell such that they protrude inwards and are later mechanically or chemically captured by the gel as it cures.

For implants with enhanced gel ("loaded" with solid particles intended, for example, to increase the cohesive strength) the above mechanisms may be used or alternatively an intermediate layer is provided comprising unloaded silicone liquid or unloaded silicone gel. The unloaded silicone gel exhibits better adhesion to the shell than loaded silicone gel because it has less cohesive strength and it has better adhesion to the loaded gel. Optionally further layers are added to the shell to compensate for the reduction in the mechanical properties of the innermost layer caused by changes to improve adhesion.

The present invention conforms to the requirements of an implantable prosthesis such as being able to provide a specific three-dimensional shape and maintain the shape for many years, preferably for the lifetime of the woman (or man, depending upon the type of surgery) in which the implant is installed to prevent the need for additional invasive surgery; having a specific feel, preferably imitating the feel of human tissue, such as the feel of a real breast; being bio-durable such that it is not ruined by interaction with the human body; being bio-compatible so that the patient's health is not detrimentally affected by the implant even under extreme circumstances: for example the filler is required to be non-toxic in case of leakage from the implant.

According to preferred embodiments of the present invention, the implant is adapted for use as a breast implant.

In an exemplary embodiment of the invention, the implant may be provided in various sizes, for example extending from 50 cc to 1500 cc or larger or smaller.

Optionally, the implant may be implanted in areas of the body other than the breast, for example to replace or augment testicles, pectorals, a chin, cheeks, a calf, buttocks or other parts of the human or an animal body, while exhibiting tactile properties similar to natural tissue. According to at least some embodiments of the present invention, a prosthetic implant, suitable for implantation to the human body, comprises a shell and a gel filling, wherein the shell comprises an innermost layer and at least an additional layer and the innermost layer is in contact with the gel and the innermost layer is adapted to adhere to the gel. Preferably the ratio of crosslinker to base polymer in the innermost layer is lower than the ratio of crosslinker to base polymer in the additional layer such that a network in formed between excess base polymer in the innermost layer that reacts with excess crosslinker in the gel to form an adhesive bond between the shell and the gel.

Alternatively the ratio of hydrogen functionalized silicone to vinyl functionalized silicone in the innermost layer is lower than the ratio of hydrogen functionalized silicone to vinyl functionalized silicone in the additional layer such that a network in formed between excess base vinyl silicones in the innermost layer that react with excess hydrogen crosslinker in the to form an adhesive bond between the shell and the gel. Preferably the ratio of hydrogen crosslinker to base vinyl silicones in the innermost shell is less than 2:1.

Alternatively the innermost layer comprises chains with bi or poly-functional groups and chains with a single functional group and wherein the resulting excess of base vinyl silicones in the innermost layer react with excess hydrogen crosslinker in the gel to form an adhesive bond between the shell and the gel. Alternatively the innermost layer comprises silicone elastomer and silicone gel to form an adhesive bond with the gel. Alternatively prior to curing of the gel, the innermost layer is wet with one part of the gel and wherein during curing of the gel inside the shell the excess the one part reacts with the curing gel to form an adhesive bond between the gel and the shell. Alternatively the innermost shell comprises a first part of a bi-component vulcanized (RTV) elastomer and wherein the gel comprises a second part of the RTV elastomer such that when the shell is filled with the gel the first and the second parts of the RTV elastomer form an adhesive bond.

Alternatively the innermost shell is wet with a first part of a bi-component vulcanized (RTV) elastomer and wherein the gel comprises a second part of the RTV elastomer such that when the shell is filled with the gel the first and the second parts of the RTV elastomer form an adhesive bond.

Alternatively the innermost shell comprises surface irregularities for adhesion to the gel. Preferably the surface irregularities comprise at least one of etches, ridges, bumps, protrusions, or indentations. Alternatively the innermost shell comprises connection elements for adhesion to the gel. Preferably the connection elements comprise at least one of fibers or hooks. Optionally the gel comprises additives to form enhanced gel and the implant comprises an intermediate layer between the innermost layer and the enhanced gel, wherein the intermediate layer comprises silicone gel or silicone liquid.

As described herein, the gel filling may be embodied in a filling containing a gel, which may for example contain other components such as particles or microspheres.

As described herein, the dispersion for the shell may be embodied in a mixture containing polymeric dispersion and other additives Although various examples are described herein, optionally the overall content of gel could only be 50% by volume for example, over the total volume of the implant.

Adhesion could be achieved by curing the innermost shell with certain additives and then using additives that would seek to attach to those shell additives in the gel. For example—the shell is impregnated with magnetic powder and the gel with metallic powder. For example, these shell and gel additives attach to each other physically, mechanically, chemically, magnetically or otherwise.

Also the additives could be only in the shell or the gel and have a mechanism to bond with the other side. For example, additives such as microspheres or similar elements that are mechanically embedded (or trapped) in the innermost layer of the shell and with part of them exposed, would crosslink with the gel.

Unless otherwise defined, all technical and scientific terms used herein have the same meaning as commonly understood by one of ordinary skill in the art to which this invention belongs. The materials, methods, and examples provided herein are illustrative only and not intended to be limiting.

Implementation of the method and system of the present invention involves performing or completing certain selected tasks or steps manually, automatically, or a combination thereof.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in order to provide what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

The present invention provides an implant which has improved adhesion between the implant shell and filling material. The implant comprises an implant material contained within a shell to form an encapsulated prosthetic implant. Several mechanisms/embodiments are disclosed below to improve the adhesion of the shell and filling gel. A non-limiting example of a suitable shell material is a silicone elastomer, optionally with a material such as polyurethane foam overlaid on the shell. At least the shell, but preferably all of the materials of the implant, is biologically compatible and safe for therapeutic and/or cosmetic use internally to the human body.

The principles and operation of the present invention may be better understood with reference to the drawings and the accompanying description.

Figure 1:
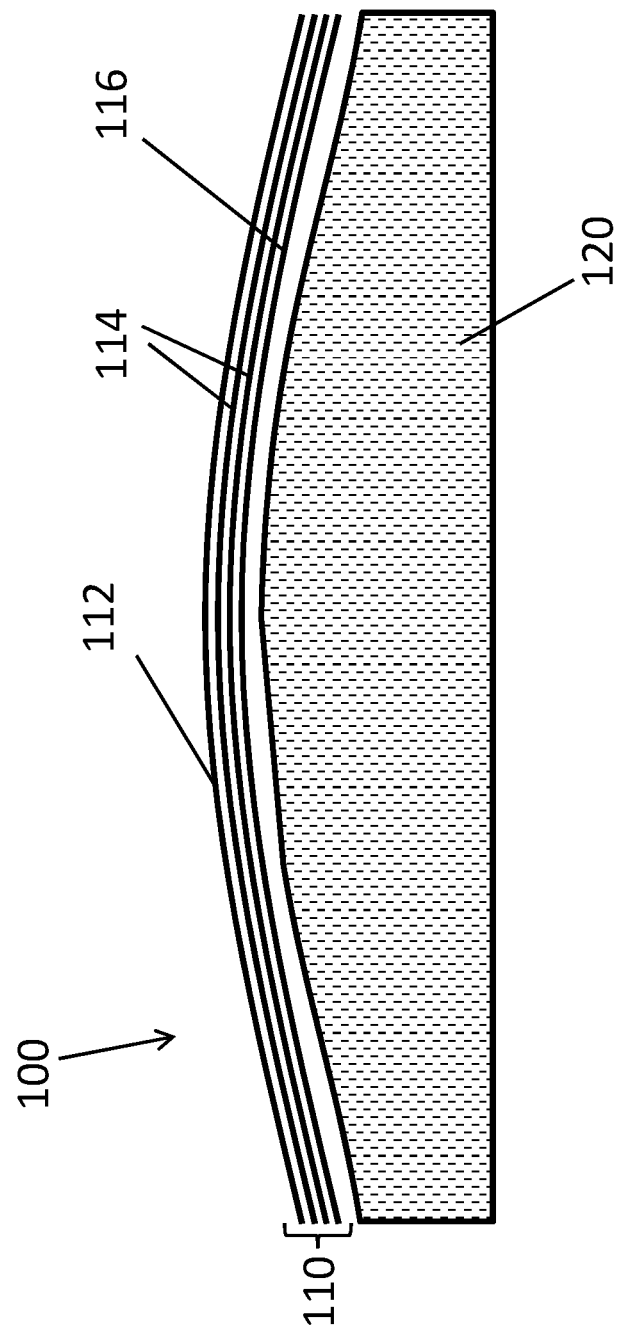
FIG. 1 is an exemplary cutaway illustration of an implant showing the shell/gel interface according to at least some embodiments of the present invention.
Figure 2:
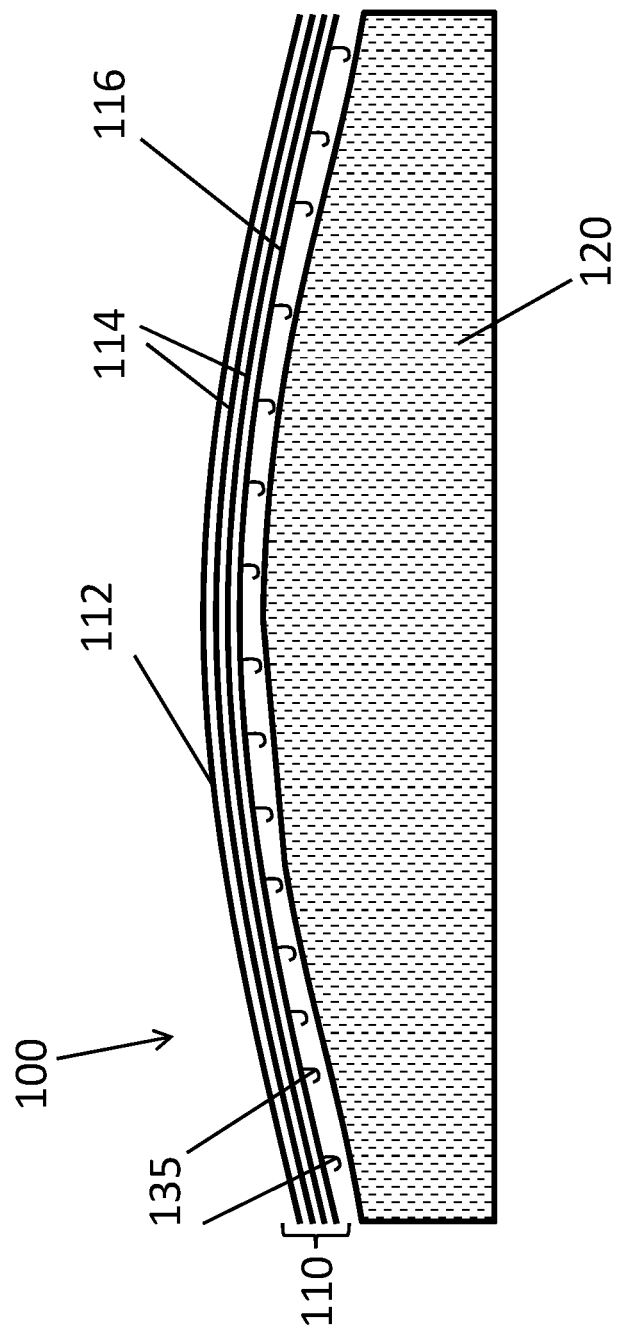
FIG. 2 is an exemplary cutaway illustration of an implant showing the shell/gel interface according to at least some embodiments of the present invention.
Figure 3:
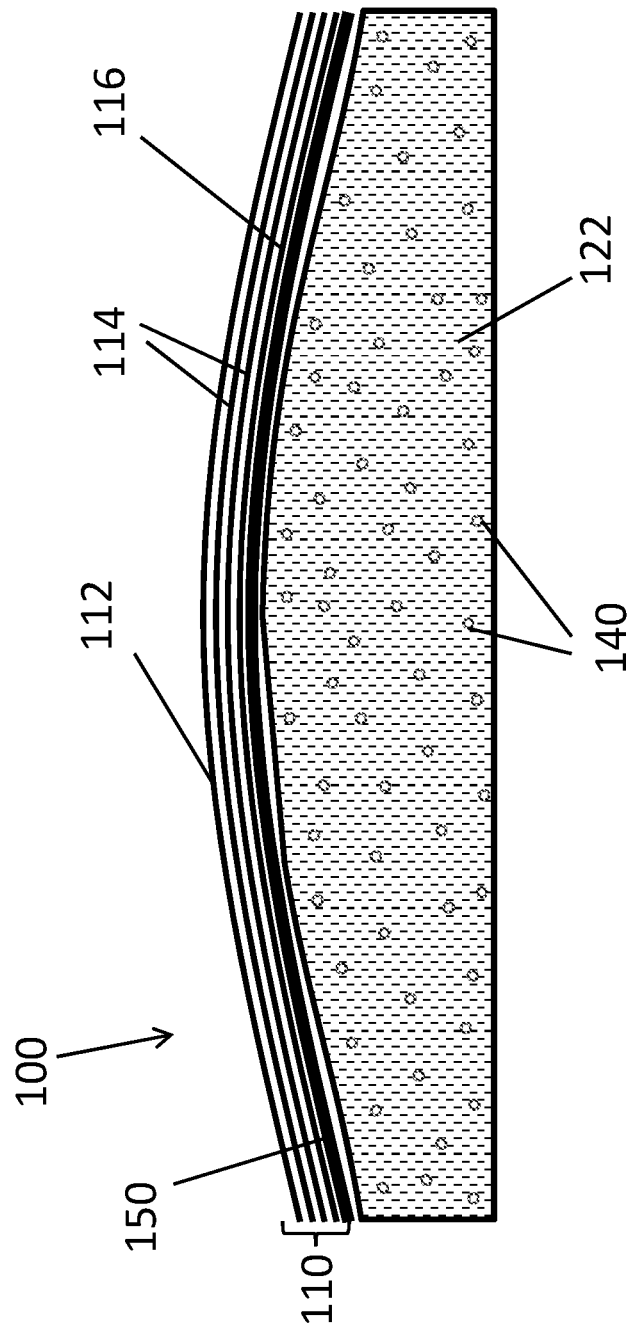
FIG. 3 is an exemplary cutaway illustration of an implant showing the shell/enhanced gel interface according to at least some embodiments of the present invention.

Reference is now made to FIGS. 1-3 which shown an exemplary cutaway illustration of an implant showing the shell/gel interface according to at least some embodiments of the present invention. The illustrations are not to scale and are provided for indicative purposes and therefore should not be considered limiting.

As shown, an implantable prosthesis 100 comprises a shell 110 that optionally comprises a biocompatible silicone, polyurethane or other material as is commonly used for implants such as PDMS (polydimethylsiloxane) and derivatives thereof for example.

Shell 110 may comprise a single layer but is shown as comprising multiple layers—specifically an outermost layer 112, inner layers 114 and innermost layer 116. Optionally some layers may be from one material and other layers from another material.

Outermost layer 112 may optionally feature any of a smooth, non-textured surface; a textured surface with various patterns; or a micro polyurethane foam coated surface. Shell 110 can have areas of varying elasticity. Shell 110 can have a different thickness in different areas. Optionally, the material of shell 110 may be a combination of several materials. Generally, shell 110 serves as an enclosure for preventing the part or all of the content of prosthesis 100 from leaking out. Optionally, shell 110 may be provided in various shapes, for example round, oval, anatomical, custom or other.

Shell 110 contains a filling material 120 which preferably comprises a silicone gel as is known in the art, such as PDMS and derivatives thereof for example, and/or any other suitable polymer gel; in the case of implanted composite 30 material the gel is biocompatible. As shown in illustrative FIG. 3, enhanced gel 122 optionally comprises dispersed solid particles 140 to create an enhanced gel with qualities such as greater cohesive strength or reduced weight.

Implant 100 comprises one or more of the following mechanisms to increase adhesion between shell 110 and gel 120. While several embodiments are disclosed it should be understood that these may be combined in any form if desired to achieve the required levels of adhesion:

In a first embodiment, the innermost layer 116 of shell 110 comprises a lower ratio of crosslinker to base polymer compared with other layers 112 and 114 such that a network in formed between excess base polymer in the shell layer 116 that reacts with the excess crosslinker in the gel 120 to form an adhesive bond between the shell and gel.

Typically, there are several differences between the shell and gel materials. A basic difference between the gel 120 and elastomer of the shell 110 is the presence of a liquid phase. An elastomer is a crosslinked network without a liquid phase and a gel is a crosslinked network that is swollen with a liquid phase. Both the elastomer and the gel are addition cured networks.

Typically crosslinked networks are formed by crosslinking polymer chains where the crosslinker may be a simple molecule or a polymer both with bi or poly-functional groups. For example, in a crosslinked silicone network formed via an addition reaction in the presence of a platinum catalyst, the base polymer contains vinyl functional groups that may react via an addition mechanism to a hydrogen functionalized crosslinker.

Another difference between gel and elastomer in a network formed via addition reaction is the ratio of vinyl functionalized silicones to hydrogen functionalized silicones used in order to form the network. Silicone elastomer contains higher ratios of hydrogen crosslinker to base vinyl silicones in order to ensure full crosslinking in a more "solid" system. An exemplary ratio is 2:1 hydrogen silicones to vinyl silicones respectively. This ensures full crosslinking to form the network that yields the desired elastomeric macroscopic mechanical properties for the shell. By contrast, silicone gel contains lower ratios of hydrogen crosslinker to base vinyl silicones which is sufficient to ensure full crosslinking in a more "liquid" system. An exemplary ratio is 1.2:1 hydrogen silicones to vinyl silicones respectively. This ensures full crosslinking to form the network that yields the desired macroscopic mechanical properties for the gel.

Further, the platinum catalyst package may or may not contain an inhibitor. Typically, the elastomer platinum catalyst does not contain an inhibitor to allow a fast and full crosslinking reaction while the gel's platinum catalyst contains an inhibitor to allow for handling of the material before it starts to crosslink.

Therefore changing the ratio of hydrogen crosslinker to base vinyl silicones in either of shell 110 or gel 120 will improve the adhesion between these, as shown in a non-limiting embodiment in Example 1. In a non-limiting example the present embodiment comprises an innermost shell 116 comprising a lower ratio of hydrogen crosslinker to base vinyl silicones compared with other layers 112 and 114. Preferably the ratio of hydrogen crosslinker to base vinyl silicones in inner shell 116 is less than 2:1.

In a further embodiment a change in ratio is achieved by an addition of a new moiety. In this embodiment the silicone dispersion of innermost layer 116 contains single vinyl silicone and bi or poly-functional vinyl silicone. Both of these compete for the hydrogen based silicone in innermost layer 116 resulting in an excess of base vinyl silicones in inner shell layer 116 which react with excess hydrogen crosslinker in gel 120 to form an adhesive bond between the shell 110 and gel 120.

In a further embodiment the innermost layer 116 of shell 110 comprises a mixed ratio of silicone elastomer and silicone gel to provide an intermediate material that is more compatible to both the elastomer shell 110 and the filling gel 120 thereby and improving adhesion to both gel 120 and elastomer 110.

A further embodiment is based on the fact that both of the gel 120 and the elastomer 110 are comprised of a two part system where one part is the base and the other part is the crosslinker as described above. Thus the innermost layer 116 of the shell 110 is wet with the base part of the gel in its liquid state or the gel in its liquid state. and these are allowed to diffuse to some extent into the innermost layer 116 and possibly into internal layers 114 of shell 110 for an extended period of time, for example but without intention to be limiting, for up to a few days before the next steps of filling and curing. During the curing process the excess of one part that is now found in the innermost layer 116 reacts with the curing gel 120 and improves the adhesion between the gel 120 and shell 110. In a further embodiment a bi-component room temperature vulcanized (RTV) elastomer is used as the adhesion promoter between shell 110 and gel 120. One component is incorporated into the elastomer 110 composition as part of the manufacturing of innermost layer 116 of the shell. The shell (comprising the part component) 110 is filled with the liquid Silicone containing the other component and upon contact with the shell 110 the two components react and create adhesion between the shell 110 and gel 120.

In a further embodiment a bi-component room temperature vulcanized (RTV) elastomer is used as the adhesion promoter between shell 110 and gel 120. One component is used to wet the shell 110 and allowed to diffuse to some extent into the internal layers 116, 114 of the shell 110 for an extended period of time, for example but without intention to be limiting, for up to a few days before the next steps of filling and curing. The shell 110 is then filled with the liquid Silicone containing the other component and upon contact with the shell 110 the two components react and create adhesion between the shell 110 and gel 120. A further embodiment is illustrated in FIG. 2 where the innermost layer 116 of shell 110 is structured or resurfaced such that the topography and chemical nature of the internal layer are altered to improve adhesion of the gel 120 to the shell 110.

The topography and chemical nature of the internal layer may be altered by means of plasma etching, chemical etching, mechanical etching, etc. to improve adhesion of the gel 120 to the shell 110.

Physical adhesion is improved by mechanical interlocking, and/or wetting properties such as lotus effect mechanisms while chemical adhesion is also improved by chemical interactions on the surface ranging from weak van der Waals (VDW) interaction to strong chemical bonds. The surface topography may be altered up to atomic, nanometric scale (peak to valley) where the surface can still be wetted by the liquid silicone.

Alternatively, the mold which is used for shell manufacturing is resurfaced by imprinting, creating a negative on the mold or mandrel surface, modifying the outermost layer of the shell and then inside-outing it, adding volatile or soluble elements on the surface that are later removed and similar methods to create the altered topography with improved adhesion for innermost layer 116.

Alternatively, layer 116 may be surfaced with macroscopic structures such as teeth, hooks, or hairs 135 to create mechanical interlocking with the gel. FIG. 2 is an illustrative drawing of such hooks or hairs 135 and should not be considered limiting. Alternatively, protruding fibers may be introduced to the shell layer 116 as an interlocking agent between the shell 110 and gel 120.

A further embodiment is provided for implants with enhanced gel 122 ("loaded" with solid particles 140 intended to increase the cohesive strength) as shown in FIG. 3. For enhanced gel 122 any one of the above mechanisms/embodiments may be used. Alternatively an intermediate layer 150 is provided comprising "unloaded" silicone liquid or unloaded silicone gel. The unloaded silicone gel 150 exhibits better adhesion to the shell 110 than loaded silicone gel 122 because it has less cohesive strength and it also has better adhesion to the loaded gel 122.

Intermediate layer 150 comprising silicone liquid is optionally formed by filling shell 110 with a volume of few cubic centimeters of silicone liquid and homogenously wetting shell 110 until a uniform silicone liquid layer is formed. A homogenous layer may, for example, be formed by rotating the shell. In order to further improve the wetting of shell 110 with silicone liquid, the liquid may be allowed to diffuse to some extent in the internal layers 114 of the shell for an extended period of time, for example but not limited to a few days before the next steps of filling the shell with the enhanced gel 122 and curing.

For any of the above embodiments where changes are made to the mechanical properties of the innermost layer 116 as a result of the changes to increase adhesion, further layers are optionally added to shell 110 to compensate for the reduction in mechanical properties.

Various non-limiting examples are now provided in regard to different embodiments of the present invention, including with regard to test results. Without wishing to be limited by a single hypothesis, among the many advantages of these embodiments there is included the improvement of adhesion between shell and gel.

Example 1—Inner Layer Modification

A typical shell is comprised of multiple layers of silicone elastomer cured successively. In this example, the innermost silicone elastomer layer in the shell was modified by varying the relative amounts of part A and part B during dispersion preparation. Different concentrations were tested. The silicone elastomer dispersion is typically mixed at a ratio of 1:1 part A-Part B. Part A contains the polymer backbone structure, such as PDMS, and a catalyst, which for example can be platinum. Part B contains the polymer backbone structure, which again could be PDMS, and a crosslinker, which for example could be hydrogen terminated as described herein. By changing the mixing ratios, the concentrations of each component in the final mix are also changed. One such changed ratio was 7.5/92.5 part B/part A respectively (described herein as 92.5% weight per weight part A to 7.5% weight per weight part B; all ratios and percentages may be considered to be given weight per weight over the entire weight of the dispersion). This inner layer modification of the shell increased adhesion of the gel to the shell of the implant.

Methods:

Three different mixtures of the dispersion were mixed for five groups as follows:
A. 90% Part A with 10% Part B (Group one)
B. 85% Part A with 15% Part B (Group two)
C. 80% Part A with 20% Part B (Group three)
D. 92.5% Part A with 7.5% Part B (Group four)
E. 50% Part A with 50% Part B (Group five)

Three shells of each group were manufactured in the following manner:
First layer featured the tested mixture of the dispersion (e.g. 90%/10%)
Followed by additional layers of dispersion as the regular mixture of 50% Part A with 50% Part B.

VI. Gel Mixing, Filling and Vulcanization of the shells:

The shells of all groups were filled with gel and vulcanized in the same manner.

Figure 4:
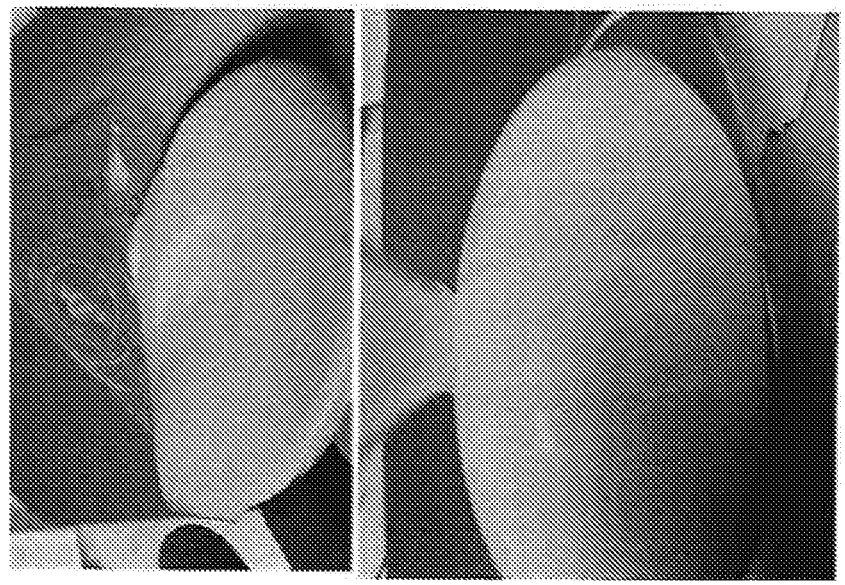
FIG. 4 shows the testing process for the visual and pull force test.

VII. Testing:

A visual and pull force test was performed as follows. About one half of the base of the shell was cut. It was pulled to see if there is any gel remaining and the amount of force needed to pull the shell from the gel. FIG. 4 shows the testing process for the visual and pull force test.

Results

For the visual and hand pull force test, the results were as follows. Visually there was no remaining gel on the shell for any of the groups tested. The forces needed to detach the gel from the shell grew with the reduction in proportion of Part B.

Example 2—Glass Bead Blasted Mold

Mandrels were surface modified by means of glass bead blasting. Different glass beads were used with sizes ranging from 0.25 to 1 mm for different mandrels. The following configurations were tested
Smooth mandrel.
0.25 mm glass bead blasted mandrel.
0.5 mm glass bead blasted mandrel.
1 mm glass bead blasted mandrel.

The mandrels used were of the same size and shape: round, high profile, 235 ml. Shells were manufactured, filled with gel and vulcanized in the same manner:

Testing:

A visual and pull force test was performed as follows. About one half of the base of the shell was cut. It was pulled to see if there was any gel remaining and the amount of force needed to pull the shell from the gel. FIG. 4 shows the testing process for the visual and pull force test.

Results

No shell-gel detachments were observed. As the glass bead size increased, the adhesion also improved. Without wishing to be limited by a single hypothesis, this is believed to be due to an increased roughness of the shell, due in turn to an increased roughness of the mandrel.

Example 3

A combination of increased surface roughness with a first layer composed of 92.5% part A and 7.5% part B was prepared and tested as per the methods described above. This combination has the best force of adhesion. It is better than that achieved without a modified layer. This is due to the increase of contact surface area combined with increased bonding between the gel and shell.

While the invention has been described with respect to a limited number of embodiments, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not described to limit the invention to the exact construction and operation shown and described and accordingly, all suitable modifications and equivalents may be resorted to, falling within the scope of the invention.

Having described a specific preferred embodiment of the invention with reference to the accompanying drawings, it will be appreciated that the present invention is not limited to that precise embodiment and that various changes and modifications can be effected therein by one of ordinary skill in the art without departing from the scope or spirit of the invention defined by the appended claims.

Further modifications of the invention will also occur to persons skilled in the art and all such are deemed to fall within the spirit and scope of the invention as defined by the appended claims.

While the invention has been described with respect to a limited number of embodiments, it will be appreciated that many variations, modifications and other applications of the invention may be made.

What is claimed is:

1. A prosthetic implant, comprising a shell and a filler containing a gel, wherein said shell comprises an innermost layer and at least one additional layer; wherein said innermost layer comprises silicone elastomer; wherein said innermost layer is in contact with said gel and said innermost layer is adapted to adhere to said gel to form an adhesive bond between said innermost layer and a layer of said gel adjacent to said innermost layer, wherein formation of said adhesive bond comprises crosslinking; wherein said implant is suitable for implantation to a human body.

2. The prosthetic implant of claim 1, wherein the innermost layer and the at least one additional layer further comprise crosslinkers and base polymers; and wherein the gel comprises crosslinker and base polymer; such that a network is formed between crosslinker and base polymer in said innermost layer that reacts with crosslinker and base polymer in said gel to form an adhesive bond between said innermost layer and said gel.

3. The prosthetic implant of claim 1 wherein the gel comprises two parts: Part A and Part B; Part A comprising silicone gel and a catalyst, and Part B comprising silicone gel and a crosslinker; wherein the silicone gel of Part A may be the same or different as the silicone gel of Part B.

4. The prosthetic implant of claim 3, wherein the ratio of Part A to Part B ranges from 95% to 5% weight per weight to 40% to 60% weight per weight.

5. The prosthetic implant of claim 3, wherein said crosslinker comprises a hydrogen crosslinker.

6. The prosthetic implant of claim 3, wherein said catalyst comprises a platinum catalyst.

7. The prosthetic implant of claim 1, wherein the innermost layer and the at least one additional layer further comprise hydrogen functionalized silicone and vinyl functionalized silicone; and wherein the gel comprises hydrogen crosslinker and vinyl functionalized base polymer; such that a network is formed between hydrogel functionalized silicone and vinyl functionalized silicone in said innermost layer that react with the hydrogen crosslinker and vinyl functionalized base polymer in said gel to form an adhesive bond between said innermost layer and said gel.

8. The prosthetic implant of claim 1, wherein the gel comprises hydrogen crosslinker; and said innermost layer further comprises chains with bi- or poly-functional groups and chains with a single functional group; and wherein the innermost layer further comprises base vinyl silicones, wherein the base vinyl silicones in said innermost layer react with hydrogen crosslinker in said gel to form an adhesive bond between said innermost layer and said gel.

9. The prosthetic implant of claim 1, wherein said innermost layer further comprises silicone gel components.

10. The prosthetic implant of claim 1, wherein said innermost layer comprises a first part of bi-component room temperature vulcanized (RTV) silicone elastomer and wherein said gel comprises a second part of said RTV silicone elastomer such that when said shell is filled with said gel said first and said second parts of said RTV silicone elastomer form an adhesive bond.

11. The prosthetic implant of claim 1, wherein said innermost layer further comprises surface irregularities for adhesion to said gel.

12. The prosthetic implant of claim 11, wherein said innermost layer comprises surface irregularities determined according to irregularities on a surface of a mandrel on which said innermost layer is constructed.

13. The prosthetic implant of claim 12, wherein said irregularities on said surface of said mandrel are determined according to impact of glass beads.

14. The prosthetic implant of claim 13 wherein said glass beads comprise up to 1 mm glass beads.

15. The prosthetic implant of claim 11, wherein said irregularities are such that the outer shell remains largely unaffected.

16. The prosthetic implant of claim 1, wherein said innermost layer comprises connection elements for adhesion to said gel.

17. A method of making the prosthetic implant of claim 1, comprising:
  i. wetting said innermost layer with one part of said gel; and
  ii. curing said gel;
wherein during the curing of said gel inside said shell, the excess of said one part reacts with the curing gel to form an adhesive bond between said gel and said innermost layer.

18. A method of making the prosthetic implant of claim 1, comprising
  i. wetting said innermost layer with a first part of bi-component room temperature vulcanized (RTV) silicone elastomer;
    wherein said gel comprises a second part of said RTV silicone elastomer such that when said shell is filled with said gel said first and second parts of said RTV silicone elastomer form an adhesive bond.

19. The prosthetic implant of claim 1, wherein formation of said adhesive bond reduces separation of the shell and the gel at the interface between the shell and the gel.

20. The prosthetic implant of claim 1, wherein said shell further comprises a biocompatible polymer selected from the group consisting of silicone and polydimethylsiloxane.

21. The prosthetic implant of claim 1, where said gel comprises a biocompatible polymer selected from the group consisting of silicone and polydimethylsiloxane.

22. The prosthetic implant of claim 1, wherein said adhesive bond is stronger than implants without an adhesive bond comprising crosslinking.

* * * * *